(12) United States Patent
Aoki et al.

(10) Patent No.: US 10,018,539 B2
(45) Date of Patent: Jul. 10, 2018

(54) SYSTEM AND METHOD FOR RETRIEVAL TREATMENT OF PROTEINS IN FORMALIN-FIXED PARAFFIN-EMBEDDED TISSUE SECTION

(71) Applicants: SHIMADZU CORPORATION, Kyoto-shi, Kyoto (JP); SHIZUOKA PREFECTURE, Shizuoka, Shizuoka (JP)

(72) Inventors: Yutaka Aoki, Nerima-ku (JP); Yukari Umino, Yokohama (JP); Taka-Aki Sato, Shinagawa-ku (JP); Isamu Hayashi, Meguro-ku (JP); Keiichi Hatakeyama, Sunto-gun (JP); Shun-ichiro Ogura, Yokohama (JP)

(73) Assignees: SHIMADZU CORPORATION, Kyoto-shi, Kyoto (JP); SHIZUOKA PREFECTURE, Shizouka, Shizuoka (JP)

( * ) Notice: Subject to any disclaimer, the term of this patent is extended or adjusted under 35 U.S.C. 154(b) by 0 days.

(21) Appl. No.: 14/978,115

(22) Filed: Dec. 22, 2015

(65) Prior Publication Data
US 2016/0153872 A1    Jun. 2, 2016

Related U.S. Application Data

(62) Division of application No. 14/119,639, filed as application No. PCT/JP2012/061090 on Apr. 25, 2012, now abandoned.

(30) Foreign Application Priority Data

May 25, 2011   (JP) ................ 2011-117334

(51) Int. Cl.
*G01N 1/30*    (2006.01)
*G01N 33/68*   (2006.01)

(52) U.S. Cl.
CPC ............... *G01N 1/30* (2013.01); *G01N 33/68* (2013.01); *G01N 33/6848* (2013.01)

(58) Field of Classification Search
CPC ...................................................... G01N 1/30
See application file for complete search history.

(56) References Cited

U.S. PATENT DOCUMENTS

| 2004/0219588 A1 | 11/2004 | Furuta |
| 2005/0130121 A1 | 6/2005 | Conklin et al. |
| 2009/0136971 A1 | 5/2009 | Krizman et al. |
| 2010/0075372 A1 | 3/2010 | Sato et al. |

FOREIGN PATENT DOCUMENTS

| JP | 2004-347594 A | 12/2004 |
| JP | 2007-514951 A | 6/2007 |
| JP | 2008-542724 A | 11/2008 |
| WO | 2008/038813 A1 | 4/2008 |

OTHER PUBLICATIONS

Jiao et al. J of Neuroscience Methods, 1999, 93:149-162.*
Djidja et al. J of Proteome Research, 2009, 8:4876-4884.*
Groseclose et al. Proteomics, 2008, 8:3715-3724 (IDS, no reference is on file) also pp. 1-19 as printed/enclosed in this office action.*
International Preliminary Report on Patentability dated Nov. 26, 2013 in International Application No. PCT/JP2012/061090.
Johan O. R. Gustafsson, et al., "Citric Acid Antigen Retrieval (CAAR) for Tryptic Peptide Imaging Directly on Archived Formalin-Fixed Paraffin-Embedded Tissue", Journal of Proteome Research, 2010, pp. 4315-4328, vol. 9, No. 9.
M. Reid Groseclose, et al., "High-throughput proteomic analysis of formalin-fixed paraffin-embedded tissue microarrays using MALDI imaging mass spectrometry", Proteomics, 2008, pp. 3715-3724, vol. 8, No. 18.
Marie-Claude Djidja, et al., "MALDI-Ion Mobility Separation-Mass Spectrometry Imaging of Glucose-Regulated Protein 78 kDa (Grp78) in Human Formalin-Fixed, Paraffin-Embedded Pancreatic Adenocarcinoma Tissue Sections", Journal of Proteome Research, 2009, pp. 4876-4884, vol. 8, No. 10.
Maurizio Ronci et al., "Protein unlocking procedures of formalin-fixed paraffin-embedded tissues: Application to MALDI-TOF Imaging MS investigations", Proteomics, 2008, pp. 3702-3714, vol. 8.
Shiurba et al. Brain Research Protocols, 1998, 2:109-119.
Bankfalvi et al. J of Pathology, 1994, 174:223-228.

* cited by examiner

*Primary Examiner* — Bin Shen
(74) *Attorney, Agent, or Firm* — Sughrue Mion, PLLC

(57) ABSTRACT

A protein retrieval treatment system used for activating proteins contained in a deparaffinized tissue section obtained by removing paraffin from a formalin-fixed paraffin embedded tissue section. The protein retrieval treatment system includes: a dispensing unit for dispensing a retrieval treatment solution over a dispensing area including a measurement area on the deparaffinized tissue section; and a moist-heat treatment unit for heating, in a saturated water vapor, the deparaffinized tissue section with the dispensing area covered with the retrieval treatment solution.

5 Claims, 4 Drawing Sheets

SYSTEM AND METHOD FOR RETRIEVAL TREATMENT OF PROTEINS IN FORMALIN-FIXED PARAFFIN-EMBEDDED TISSUE SECTION

CROSS REFERENCE TO RELATED APPLICATIONS

This application is a Divisional of U.S. application Ser. No. 14/119,639, filed Mar. 5, 2014, which is a National Stage of International Application No. PCT/JP2012/061090 filed Apr. 25, 2012, claiming priority based on Japanese Patent Application No. 2011-117334 filed May 25, 2011, the contents of all of which are incorporated herein by reference in their entirety.

TECHNICAL FIELD

The present invention relates to a system and method for a retrieval treatment of proteins contained in a formalin-fixed paraffin-embedded tissue section obtained by a formalin-fixing treatment followed by a paraffin-embedding treatment (such a tissue section is hereinafter called the "paraffin-embedded tissue section"), and more specifically, to a retrieval treatment system and method for pretreating the aforementioned tissue section in advance of a mass spectrometry.

BACKGROUND ART

In recent years, the bio-imaging technique for imaging a distribution of biological substances (such as proteins or metabolites) in a section of biological tissue has been used in the fields of clinical diagnoses or drug discoveries. In particular, this technique is widely used for an investigation of a distribution of biological substances, in which a section sample prepared by an appropriate pretreatment of a paraffin-embedded tissue section is scanned by a MALDI (matrix-assisted laser desorption ionization) mass spectrometer, and the thereby measured masses of biological substances in the section sample are comprehensively analyzed to determine the distribution of the biological substances.

A pretreating method described in Non-Patent Documents 1, 2, 3 and 4 has conventionally been used to make a paraffin-embedded tissue section available as a section sample for a mass spectrometry. This conventional pretreatment method is hereinafter described by means of the flowchart shown in FIG. 2.

Initially, paraffin is removed from the paraffin-embedded tissue section, after which a hydration treatment is performed to obtain a deparaffinized tissue section (S1). Inside the molecules of the proteins contained in the deparaffinized tissue section thus obtained, bonding of single amino acid residues or a formation of methylene crosslink by a hydroxyl group, in particular, a strong methylene crosslink via a primary amino or phenyl radical, have occurred. To dissociate such bonds or crosslinks (both are referred to as "crosslinks" hereinafter), the tissue section is subjected to a heat treatment in a retrieval treatment solution (S2: this treatment is hereinafter called the "retrieval treatment"). Subsequently, the retrieval treatment solution which has adhered to the deparaffinized tissue section during the retrieval treatment is washed off (S3). After the washing, the deparaffinized tissue section is treated with a digestive enzyme, such as trypsin, to hydrolyze proteins contained in the tissue section into peptides (S4). Lastly, after the enzymatic treatment, a matrix solution is dropped onto the deparaffinized tissue section to deposit the matrix on it (S5). The section sample thus prepared is subjected to the MALDI mass spectrometry.

The retrieval treatment in the previously described conventional pretreatment method is not only indispensable for restoring two-dimensional and three-dimensional structures of the protein molecules which have been damaged due to the crosslinking reaction caused by the formalin fixation treatment, but also for facilitating an approach of the digestive enzyme to protein molecules in the subsequent enzymatic treatment. In one conventional retrieval treatment, the deparaffinized tissue section is immersed in a retrieval treatment solution containing a surfactant, and a heat treatment (in a hot bath, a microwave oven or an autoclave) is performed on the immersed sample for a predetermined period of time.

BACKGROUND ART DOCUMENT

Non-Patent Document

Non-Patent Document 1: Maurizio Ronci, Elena Bonanno, Alfredo Colantoni, Luisa Pieroni, Carmine Di Ilio, Luigi Giusto Spagnoli, Giorgio Federici and Andrea Urbani, "Protein unlocking procedures of formalin-fixed paraffin-embedded tissues: Application to MALDI-TOF Imaging MS investigations", Proteomics, vol. 8, 2008, pp. 3702-3714

Non-Patent Document 2: M. Reid Groseclose, Pierre P. Massion, Pierre Chaurand, and Richard M. Caprioli, "High-throughput proteomic analysis of formalin-fixed paraffin-embedded tissue microarrays using MALDI imaging mass spectrometry", Proteomics, Vol. 8, No. 18, 2008, pp. 3715-3724

Non-Patent Document 3: Marie-Claude Djidja, Emmanuelle Claude, Marten F. Sne, Peter Scriven, Simona Francese, Vikki Carolan and Malcolm R. Clench, "MALDI-Ion Mobility Separation-Mass Spectrometry Imaging of Glucose-Regulated Protein 78 kDa (Grp78) in Human Formalin-Fixed, Paraffin-Embedded Pancreatic Adenocarcinoma Tissue Sections", Journal of Proteome Research, Vol. 8, No. 10, 2009, pp. 4876-4884

Non-Patent Document 4: Johan O. R. Gustafsson, Martin K. Oehler, Shaun R. McColl and Peter Hoffmann, "Citric Acid Antigen Retrieval (CAAR) for Tryptic Peptide Imaging Directly on Archived Formalin-Fixed Paraffin-Embedded Tissue", Journal of Proteome Research, Vol. 9, No. 9, 2010, pp. 4315-4328

SUMMARY OF THE INVENTION

Problem to be Solved by the Invention

However, when the deparaffinized tissue section is immersed in the retrieval treatment solution, a portion of the biological substances in the deparaffinized tissue section flows into the retrieval treatment solution and is lost. The loss of biological substances from the tissue section also occurs in the process of washing off the retrieval treatment solution adhered to the deparaffinized tissue section after the retrieval treatment. As a result, when a section sample prepared through the conventional retrieval treatment is subjected to a MALDI mass spectrometry, the intensities of the peaks originating from the biological substances become low, making the result of a quantitative determination incorrect or preventing a qualitative analysis of a trace amount of component. Such a situation leads to the problem that, when an image mapping is performed based on the result of the MALDI mass spectrometry, it is difficult to create a mapping image with a sufficient amount of information for correctly reflecting the true concentrations of the biological substances.

Thus, the problem to be solved by the present invention is to provide a system and method for a retrieval treatment of proteins in a deparaffinized tissue section in which the loss of biological substances from the tissue section does not occur in the process of activating the proteins in the deparaffinized tissue section, and therefore, the peaks can be detected with adequate intensities that cause no problems in a quantitative or qualitative analysis in a MALDI mass spectrometry, so that a larger amount of information is available for the image mapping.

Means for Solving the Problem

A system for a retrieval treatment of proteins in a deparaffinized tissue section according to the present invention aimed at solving the previously describe problem is a protein retrieval treatment system for retrieval of protein molecules in a measurement area on a deparaffinized tissue section prepared by removing paraffin from a formalin-fixed paraffin-embedded tissue section obtained by a formalin-fixing treatment followed by a paraffin-embedding treatment, the retrieval being performed for a mass spectrometry of the measurement area and achieved by dissociating a crosslink resulting from formalin fixation in the protein molecules contained in the measurement area, and the system including:

a dispensing unit for dispensing a retrieval treatment solution over a dispensing area including the measurement area on the deparaffinized tissue section; and a moist-heat treatment unit for heating, by using a saturated water vapor, the deparaffinized tissue section with the retrieval treatment solution put on the dispensing area.

The system for a retrieval treatment of proteins in a deparaffinized tissue section according to the present invention is designed so as to exclude, from the retrieval treatment, the conventional process of immersing the deparaffinized tissue section in a retrieval treatment solution and washing the tissue section after the immersing. After a retrieval treatment solution is dispensed in the dispensing unit onto the deparaffinized tissue section, the deparaffinized tissue section is subjected to the moist-heat treatment. To make this treatment as effective as the process of immersing the deparaffinized tissue section in a retrieval treatment solution, the retrieval treatment solution should preferably contain a surfactant. Adding a surfactant to the retrieval treatment solution improves the affinity between the retrieval treatment solution and the deparaffinized tissue section, so that the crosslink resulting from the formalin fixation can be adequately dissociated when subjected to the moist-heat treatment.

In the previously described retrieval treatment system, the dispensing unit may dispense the retrieval treatment solution at predetermined space intervals so as to form a plurality of droplets separated from each other within the dispensing area.

In this case, the volume of each of the droplets and the space intervals of the droplets should preferably be set so that the dispensing area is covered with the plurality of droplets.

The dispensing unit may be configured so that it dispenses the retrieval treatment solution a plurality of times onto the same spot within the dispensing area.

A method for a retrieval treatment of proteins in a deparaffinized tissue section according to the present invention aimed at solving the previously described problem is a protein retrieval treatment method for retrieval of protein molecules in a measurement area on a deparaffinized tissue section prepared by removing paraffin from a formalin-fixed paraffin-embedded tissue section obtained by a formalin-fixing treatment followed by a paraffin-embedding treatment, the retrieval being performed for a mass spectrometry of the measurement area and achieved by dissociating a crosslink resulting from formalin fixation in protein molecules contained in the measurement area, and the method including:

a dispensing process in which a retrieval treatment solution is dispensed over a dispensing area including the measurement area on the deparaffinized tissue section; and a moist-heat treatment process in which the deparaffinized tissue section with the retrieval treatment solution put on the dispensing area is heated by using a saturated water vapor.

In the dispensing process of the previously described invention, the retrieval treatment solution may be dispensed at predetermined space intervals so as to form a plurality of droplets separated from each other within the dispensing area.

In this case, the volume of each of the droplets and the space intervals of the droplets should preferably be set so that the dispensing area is covered with the plurality of droplets.

In the dispensing process, the retrieval treatment solution may be dispensed a plurality of times onto the same spot within the dispensing area.

The pH of the retrieval treatment solution may be equal to or higher than 9.

Effect of the Invention

In the system and method for a retrieval treatment of proteins in a deparaffinized tissue section according to the present invention, the loss of biological substances from the deparaffinized tissue section due to the immersing does not occur, since the deparaffinized tissue section is not immersed in a retrieval treatment solution as in the conventional case; instead, the retrieval treatment solution is dispensed on the deparaffinized tissue section before the moist-heat treatment is performed. Furthermore, since the washing process which has conventionally been needed after the retrieval treatment is omitted, the loss of biological substances from the deparaffinized tissue section due to the washing does not occur. Accordingly, the actual amounts of biological substances will be correctly reflected in the peak intensities, so that the peak intensities obtained by a MALDI mass spectrometry will be higher than in the conventional case. The increase in the peak intensities leads to an increased number of peaks whose chemical structures can be identified by a qualitative analysis as well as an improved detection limit in a quantitative analysis. As a result, a more accurate mapping image with a greater amount of information can be created.

MODE FOR CARRYING OUT THE INVENTION

Figure 1:
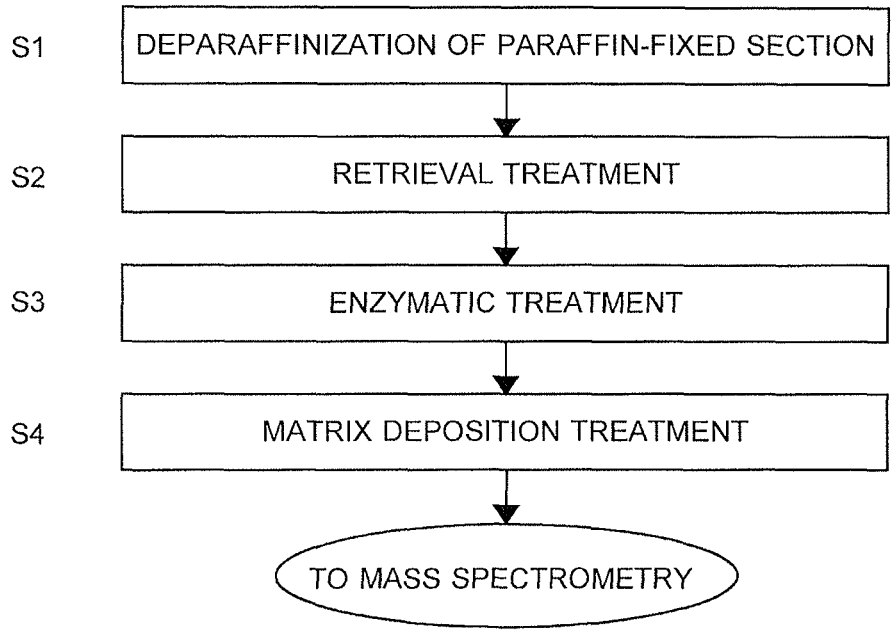
FIG. 1 is a flowchart showing a method of pretreating a paraffin-embedded tissue section by using a retrieval treatment system according to the present invention.
Figure 2:
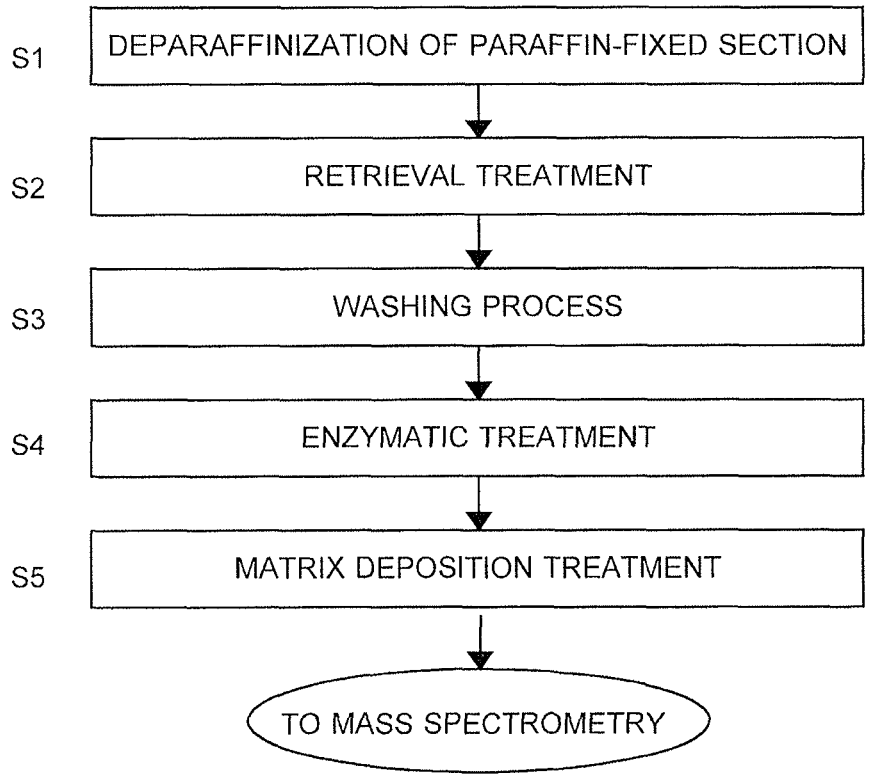
FIG. 2 is a flowchart showing a method of pretreating a paraffin-embedded tissue section by using a conventional retrieval treatment method.
Figure 3:
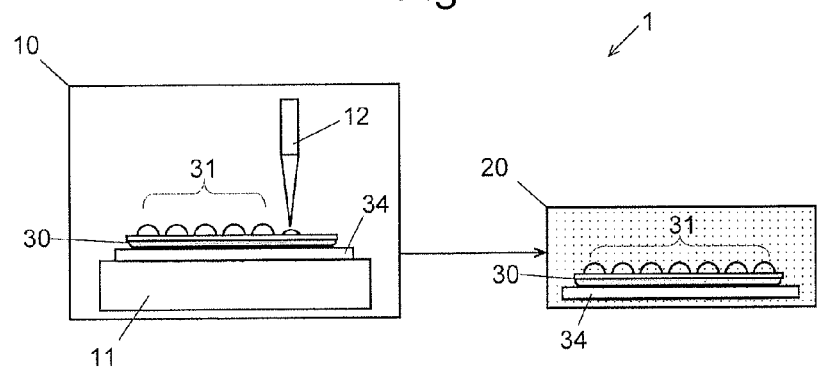
FIG. 3 is a configuration diagram showing the main components of a retrieval treatment system according to one embodiment of the present invention.

One embodiment of the system for a retrieval treatment of proteins in a deparaffinized tissue section according to the present invention is hereinafter described with reference to the attached drawings (the system is hereinafter simply called the "retrieval treatment system"). FIG. 3 is a configuration diagram showing the main components of the retrieval treatment system 1 according to the present embodiment.

The retrieval treatment system 1 is composed of a dispensing unit 10 for dispensing a retrieval treatment solution onto a deparaffinized tissue section 30 and a moist-heat treatment unit 20 for heating, in a saturated water vapor, the deparaffinized tissue section 30 with a retrieval treatment solution 31 put on it.

The dispensing unit 10 includes: a platform 11 on which a sample plate 34 with the deparaffinized tissue section 30 put thereon is to be placed, a solution storage container (not shown) for holding a retrieval treatment solution, and a dispenser 12 for dispensing the retrieval treatment solution.

In the moist-heat treatment unit 20, a sample plate 34 carrying the deparaffinized tissue section 30 with the retrieval treatment solution 31 put thereon is loaded in a pressure-resistant container, and the deparaffinized tissue section 30 is heated with a saturated water vapor at a predetermined temperature for a predetermined period of time.

As the dispensing unit 10, any dispensing device capable of dispensing a trace amount of solution onto a specified area can be used. A particularly suitable example is a chemical printer CHIP-1000 (manufactured by Shimadzu Corporation), which is capable of dispensing a picoliter-size droplet. As the moist-heat treatment unit 20, an autoclave can suitably be used.

The dispensing unit 10 and the moist-heat treatment unit 20 may be provided separately from each other or integrally as a single unit. The dispensing unit 10 can not only be used for dispensing the retrieval treatment solution but also for applying a predetermined treatment solution to the deparaffinized tissue section 30 in the subsequent enzymatic treatment and the matrix deposition treatment.

EXAMPLE

One example of the method for a retrieval treatment of proteins in a deparaffinized tissue section, which was performed by the previously described retrieval treatment system 1, is hereinafter described (this method is hereinafter simply called the "retrieval treatment method"). In the present example, the retrieval treatment was performed under a plurality of dispensing conditions in order to find an optimum dispensing amount of the retrieval treatment solution.

In the present example, the aforementioned chemical printer CHIP-1000 was used as the dispensing unit 10 of the retrieval treatment system 1, and the autoclave KS-243 (manufactured by TOMY SEIKO CO., LTD) was used as the moist-heat treatment unit 20.

Figure 4A:
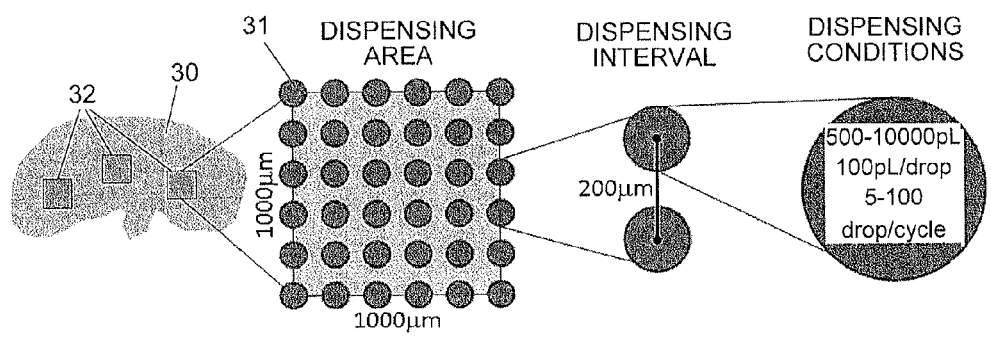
FIG. 4A is a model diagram illustrating a retrieval treatment according to one example of the present invention.

A piece of kidney tissue of a mouse was fixed with formalin, after which the tissue was embedded in paraffin and sliced to obtain a formalin-fixed paraffin-embedded kidney tissue section (3 µm thick). Then, the tissue section was laid on an electrically conductive support and dried. The obtained formalin-fixed paraffin-embedded kidney tissue section was exposed to xylene at room temperature for 30 minutes to remove paraffin and obtain a deparaffinized kidney tissue section 30. Subsequently, as a hydration treatment, the deparaffinized kidney tissue section 30 was sequentially exposed to 100% ethanol (twice), 90% ethanol, 80% ethanol and 70% ethanol, 10 seconds in each. After the hydration treatment, the deparaffinized kidney tissue section 30 was put on a sample plate for slide glass and set in the chemical printer CHIP-1000. As the retrieval treatment solution, a 0.1% n-octyl-β-D-glucoside solution/10 mM Tris-HCl (pH 10.0) solution was put in the solution storage container. Furthermore, as shown in FIG. 4A, the retrieval treatment solution 31 was dispensed at intervals of 200 µm within each of a plurality of 1000-µm square dispensing areas 32 on the deparaffinized kidney tissue section 30. That is to say, six spots were set at intervals of 200 µm on each side of one dispensing area 32, and the retrieval treatment solution 31 was dispensed onto a total of 36 spots (6 spots×6 spots).

To find an optimum dispensing amount, the measurement was performed under 11 conditions with different dispensing amount per spot: 500 pL, 1000 pL, 2000 pL, 2500 pL, 3000 pL, 3500 pL, 4000 pL, 4500 pL, 5000 pL, 7500 pL and 10000 pL. The volume of the retrieval treatment solution dispensed onto each spot was adjusted as desired by dropping an appropriate number of 100-pL droplets according to the required quantity (e.g., for a spot onto which a total of 2500 pL must be dispensed, a 100-pL droplet was dropped 25 times onto the tissue).

After the dispensing process, the deparaffinized kidney tissue section 30 was put in a stainless box together with wet paper material and subjected to a moist-heat treatment in the autoclave at 110 degrees Celsius for 10 minutes.

After the moist-heat treatment, the deparaffinized kidney tissue section 30 was once more set in the chemical printer CHIP-1000. As an enzymatic treatment solution, a 100 µg/mL trypsin/10 mM ammonium bicarbonate/5% isopropanol solution was put in the solution storage container. A total of 5000 pL of the enzymatic treatment solution was dispensed onto every spot where the retrieval treatment solution 31 had been dispensed, after which the tissue section was left in a thermostatic chamber at 37 degrees Celsius for 180 minutes to hydrolyze proteins contained in the dispensing area 32 of the deparaffinized kidney tissue section 30. Then, as a matrix solution, a 50 mg/mL 2,5-dihydroxy benzoic acid/50% acetonitrile/0.1% trifluoroacetic acid solution was put in the solution storage container and dispensed at intervals of 150 µm with a total of 7500 pL for each dispensing spot so as to deposit 2,5-dihydroxy benzoic acid on the deparaffinized kidney tissue section 30. The section sample thus obtained was subjected to a MALDI mass spectrometry. The conditions of the MALDI mass spectrometry will be described later.

The retrieval treatment solution used in the previously described retrieval treatment was adjusted at pH 9.6. Biasing the pH of the retrieval treatment solution toward the basic side in this manner improves the reaction rate of the hydrolysis of proteins by trypsin in the subsequent enzymatic treatment since trypsin has an weakly-basic optimum pH (from pH 8 to 9).

COMPARATIVE EXAMPLE

As a comparative example, a formalin-fixed paraffin-embedded kidney tissue section of a mouse was treated as follows based on the conventional method.

The deparaffinized kidney tissue section 30 which had undergone the deparaffinization and hydration treatments in the same manner as in the previous example was immersed in a retrieval treatment solution having the same composition as in the previous example and subjected to a moist-heat treatment in the autoclave at 110 degrees Celsius for 10 minutes. After the moist-heat treatment, the deparaffinized kidney tissue section 30 was taken out from the retrieval treatment solution and immersed in 70% ethanol for five minutes to adequately wash the deparaffinized kidney tissue section 30. After the washing, the enzymatic treatment and the matrix deposition treatment of the deparaffinized kidney tissue section 30 were performed under the same conditions as in the previous example. The obtained section sample was subjected to a MALDI mass spectrometry under the same measurement conditions as in the previous example.

Figure 4B:
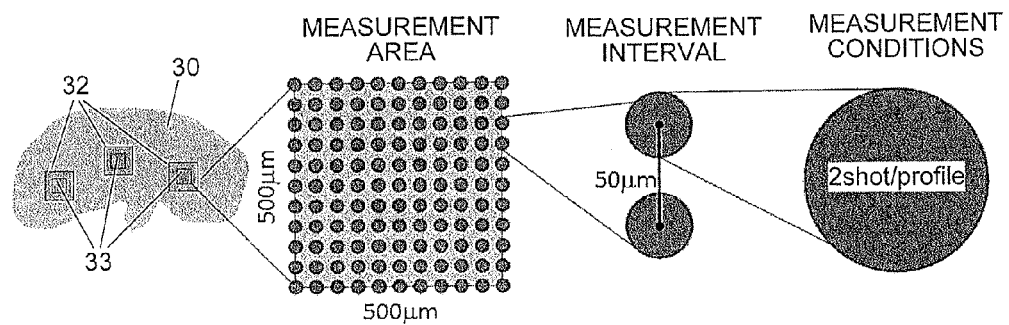
FIG. 4B is a model diagram illustrating a MALDI mass spectrometry according to the present example.

For each of the section samples in the present example and the comparative example, a MALDI mass spectrometry was performed under the following conditions:
Device: Matrix-assisted laser desorption/ionization time-of-flight mass spectrometer AXIMA-QIT (manufactured by Shimadzu Corporation)
Laser: 5 Hz, 2 shots/point
Space intervals of irradiation: 50 µm
Ion polarity: positive
Mode of measurement mass area: MID MASS
Mass range to be measured: m/z 700-2500
Measurement area: 500 µm×500 µm
Measurement points: 11×11=121 points As schematically shown in FIG. 4B, for each of the 121 points arranged at intervals of 50 µm within each of the 500-µm square measurement areas 33 included in the dispensing area 32, the MALDI mass spectrometry was performed by irradiating two shots of laser beam at each point.

Within the aforementioned mass range to be measured, the peak intensity at each mass-to-charge ratio was acquired. The minimum intensity of the 100 peaks on both sides of each detection peak was regarded as the background for that peak and subtracted from the peak intensity. After that, each peak intensity was corrected by being divided by the total of all the peak intensities. Each peak detected in the present example was compared with the peak detected at the same mass-to-charge ratio in the comparative example, and those detection peaks were selected whose intensities were equal to or higher than two times those of the comparative example and which were statistically significant ($p<0.05$).

The results of the MALDI mass spectrometry are hereinafter described.

Figure 5:
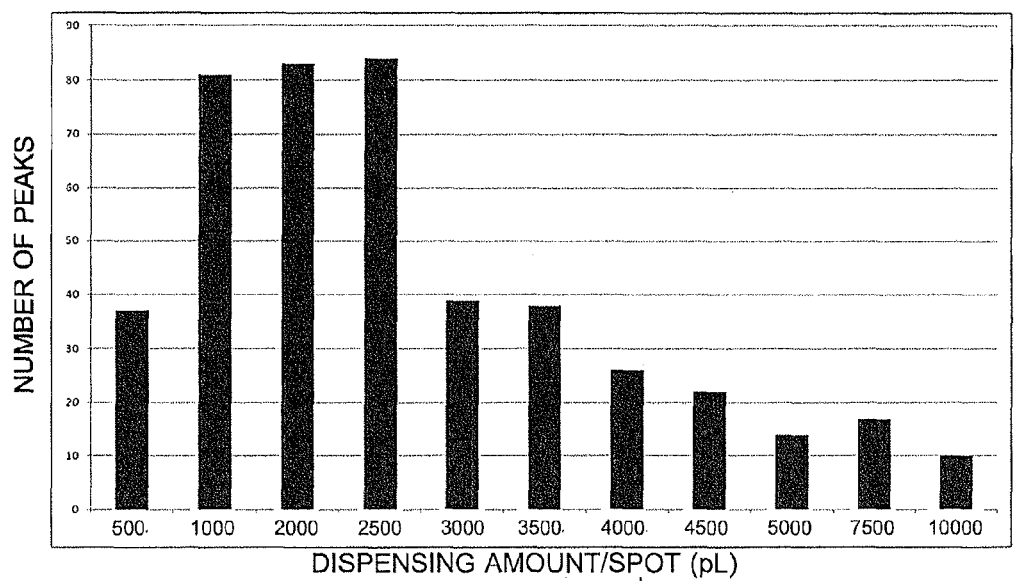
FIG. 5 is a bar graph showing the number of detected peaks with respect to the dispensing amount of the retrieval treatment solution.

FIG. 5 is a graph showing the number of detected peaks with respect to the dispensing amount of the retrieval treatment solution in the present example. The number of detected peaks showed the tendency of increasing with the dispensing amount of the retrieval treatment solution until the amount reaches 1000 pL. The number of detected peaks at a dispensing amount of 1000 pL was approximately two times the value at a dispensing amount of 500 pL. The number of detected peaks did not significantly increase while the dispensing amount was within a range from 1000 pL to 2500 pL. These results demonstrate that 500 pL is not a sufficient volume of the retrieval treatment solution for activating proteins in the dispensing area 32, while the proteins in the dispensing area 32 can be adequately activated when the dispensing amount is 1000 pL or more.

On the other hand, the number of detected peaks dramatically decreased after the dispensing amount of the retrieval treatment solution exceeded 3000 pL. A probable reason is that, when the dispensing amount of the retrieval treatment solution exceeds a certain level, the droplets of the retrieval treatment solution formed on the deparaffinized kidney tissue section 30 become combined with each other, causing the retrieval treatment solution to flow to the outside of the dispensing area 32, so that the biological substances which have been transferred into the retrieval treatment solution are lost from the dispensing area 32.

To support this reasoning, the deparaffinized kidney tissue section 30 after the dispensing process was visually examined in the two cases where the dispensing amount of the retrieval treatment solution per spot was 2500 pL and 5000 pL, respectively. It was confirmed that, in the case of the dispensing amount of 2500 pL, the droplet at each spot retained a good shape, whereas, in the case of the dispensing amount of 5000 pL, the droplets at the neighboring spots were combined together, causing the retrieval treatment solution to flow to the outside of the dispensing area 32.

From these results, it can be said that the dispensing amount per spot should be 2500 pL or less so that the retrieval treatment solution can be dispensed in the form of separate droplets.

Figure 6:
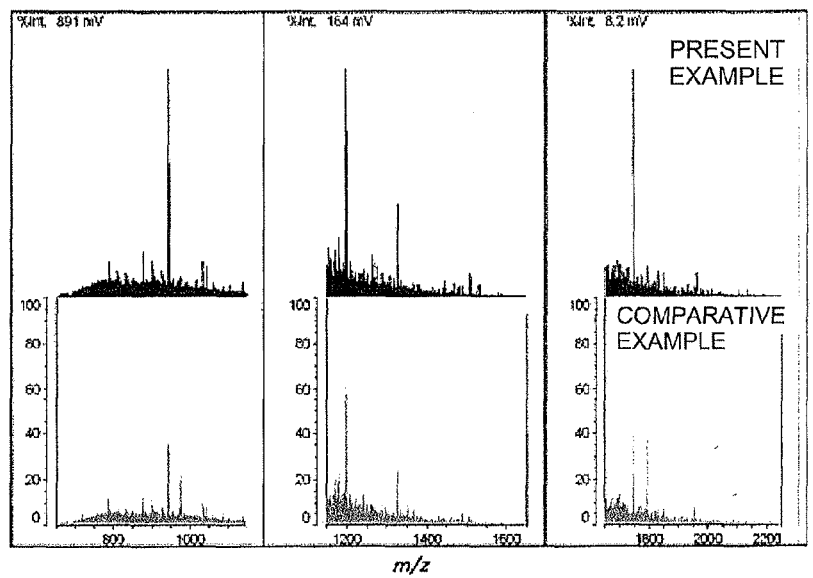
FIG. 6 shows mass peak profiles obtained in the present example and in a comparative example for each of the predetermined mass ranges.

FIG. 6 shows mass peak profiles obtained in the present example in which the retrieval treatment solution was dispensed with a volume of 2500 pL each spot (i.e. by the largest possible dispensing amount within a range where the droplets of the retrieval treatment solution can retain a good shape) and those obtained in the comparative example, with each profile showing one of the three predetermined mass ranges of m/z 750-1150, m/z 1150-1650 and m/z 1650-2250. The profiles of the present example generally show a larger number of clear peaks than those of the comparative example. This tendency is particularly noticeable within the mass range of m/z 1650-2250.

Figure 7:
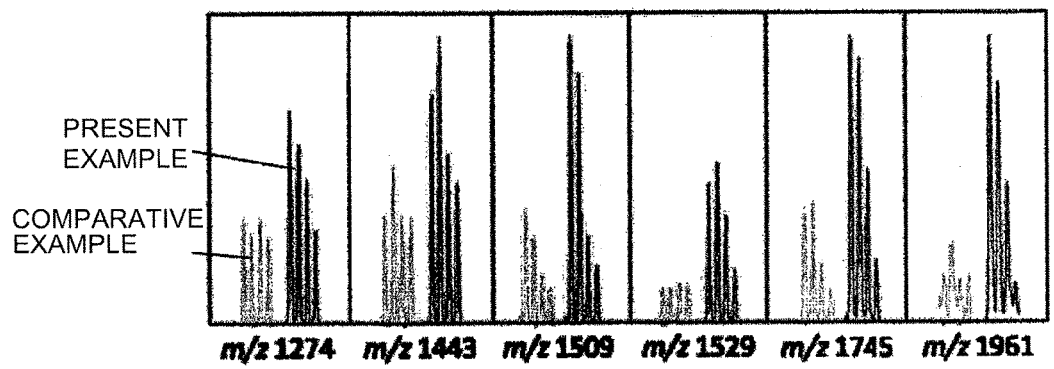
FIG. 7 shows enlarged views of major peaks detected in the present example and in the comparative example, where the thicker and thinner lines correspond to the present example and the comparative example, respectively.

FIG. 7 shows enlarged views of representative peaks (detected at m/z 1274, m/z 1443, m/z 1509, m/z 1529, m/z 1745 and m/z 1961) extracted from the mass peak profiles of FIG. 6. The thicker lines show the peaks obtained in the present example in which the retrieval treatment solution was dispensed with a volume of 2500 pL each spot, while the thinner lines show the peaks obtained in the comparative example. At any of those m/z values, the intensities of the peaks detected in the present example were equal to or higher than two times the corresponding peaks detected in the comparative example.

Figure 8:
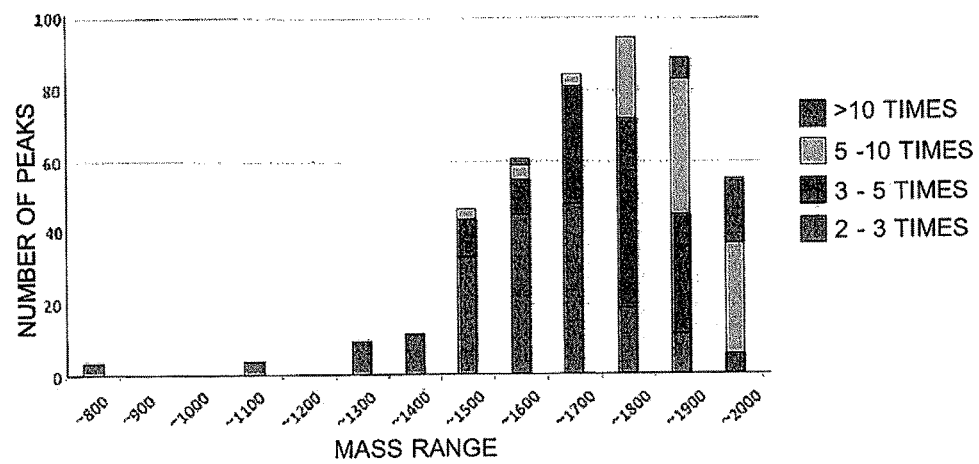
FIG. 8 is a bar graph showing, for each mass range, the intensity ratios of the peaks detected in the present example to those of the peaks detected in the comparative example.

FIG. 8 specifically shows, for each mass range, peak-intensity ratios of 461 peaks which were extracted from the peaks detected in the MALDI mass spectrometry of the section sample obtained in the present example in which the retrieval treatment solution was dispensed with a volume of 2500 pL each spot, and each of which had a peak intensity equal to or higher than two times the peak detected at the same mass-to-charge ratio in the comparative example. A peak detected at a higher mass-to-charge ratio had a tendency to have a higher peak-intensity ratio. In the aforementioned 461 peaks, 182 peaks (39.5%) had their intensities improved to 2-3 times the levels in the comparative example, 149 peaks (32.3%) had their intensities improved to 3-5 times, 104 peaks (22.6%) had their intensities improved to 5-10 times, and 26 peaks (5.6%) had their intensities improved to higher than 10 times.

As described thus far, by using the retrieval treatment system and retrieval treatment method according to the present invention, a larger number of peaks will be detected with a higher detection sensitivity in a MALDI mass spectrometry than in the case where the retrieval treatment is performed by the conventional method. This is probably because the conventional process of immersing the sample in the retrieval treatment solution and subsequently washing the sample is omitted, and therefore, the loss of biological substances from the deparaffinized tissue section is avoided. Furthermore, it is expected that the molecules of the biological substances and those of the components of the retrieval treatment solution frequently collide with each other inside the micro-sized droplets of the retrieval treatment solution during the moist-heat treatment. This phenomenon probably promotes the retrieval and thereby improves the detection sensitivity.

It should be noted that the specific forms of the present invention described thus far do not limit the present invention. For example, although the dispensing areas and the measurement areas shown in the drawings were shaped rectangular, they may have any other shapes, such as a circular shape. Various other changes can be made without departing from the spirit of the present invention.

EXPLANATION OF NUMERALS

1 . . . Retrieval Treatment System
10 . . . Dispensing Unit
11 . . . Platform
12 . . . Dispenser
20 . . . Moist-Heat Treatment Unit
30 . . . Deparaffinized Tissue Section
31 . . . Retrieval Treatment Solution
32 . . . Dispensing Area
33 . . . Measurement Area
34 . . . Sample Plate

The invention claimed is:

1. A protein retrieval treatment method comprising:
putting a methylene crosslink dissociation treatment solution on a dispensing area including a measurement area for a mass spectrometry on a deparaffinized tissue section prepared by removing paraffin from a formalin-fixed paraffin-embedded tissue section obtained by a formalin-fixing treatment followed by a paraffin-embedding treatment, wherein the methylene crosslink dissociation treatment solution is put on the dispensing area such that the deparaffinized tissue section is not immersed in the methylene crosslink dissociation treatment solution; and
heating the deparaffinized tissue section with the methylene crosslink dissociation treatment solution put on the dispensing area by using a saturated water vapor and thereby dissociating a crosslink resulting from formalin fixation in protein molecules contained in the measurement area.

2. The protein retrieval treatment method according to claim 1, wherein the methylene crosslink dissociation treatment solution is dispensed at predetermined space intervals so as to form a plurality of droplets separated from each other within the dispensing area.

3. The protein retrieval treatment method according to claim 2, wherein a volume of each of the droplets and the space intervals of the droplets are set so that the dispensing area is covered with the plurality of droplets.

4. The protein retrieval treatment method according to claim 1, wherein the methylene crosslink dissociation treatment solution is dispensed a plurality of times onto a same spot within the dispensing area.

5. The protein retrieval treatment method according to claim 1, wherein a pH of the methylene crosslink dissociation treatment solution is equal to or higher than 9.

* * * * *